(12) United States Patent
Campbell, Sr.

(10) Patent No.: US 6,505,624 B1
(45) Date of Patent: Jan. 14, 2003

(54) GAS DELIVERY SYSTEM RETENTION DEVICE AND METHOD FOR RETAINING A GAS DELIVERY SYSTEM

(76) Inventor: George Campbell, Sr., 1011 E. Tonopah Dr., Phoenix, AZ (US) 85024

( * ) Notice: Subject to any disclaimer, the term of this patent is extended or adjusted under 35 U.S.C. 154(b) by 0 days.

(21) Appl. No.: 10/059,830

(22) Filed: Jan. 29, 2002

(51) Int. Cl.[7] ............................ A61M 15/08; A62B 7/00
(52) U.S. Cl. ............................ 128/207.18; 128/207.17; 128/DIG. 26
(58) Field of Search ................. 126/200.26, 207.14, 126/207.18, DIG. 26, 207.17; 604/174, 177; 381/187; 179/156 A; 128/206.13, 201.11

(56) References Cited

U.S. PATENT DOCUMENTS

| | | | | |
|---|---|---|---|---|
| 2,245,969 A | * | 6/1941 | Francisco et al. | 128/207.18 |
| 3,836,732 A | * | 9/1974 | Johanson et al. | 179/107 |
| 3,975,599 A | * | 8/1976 | Johanson | 179/107 |
| 3,993,879 A | * | 11/1976 | Larkin | 179/156 |
| 4,118,606 A | * | 10/1978 | Larkin | 179/156 |
| 4,195,918 A | * | 4/1980 | Freche et al. | 351/158 |
| 4,335,281 A | * | 6/1982 | Scott et al. | 179/156 |
| 4,465,067 A | * | 8/1984 | Koch et al. | 128/207.18 |
| 4,617,431 A | * | 10/1986 | Scott et al. | 179/156 |
| 4,720,857 A | * | 1/1988 | Burris et al. | 379/430 |
| 4,864,610 A | * | 9/1989 | Stevens | 379/431 |
| 4,878,491 A | * | 11/1989 | McGilvray, III | 128/201.11 |
| 4,893,344 A | * | 1/1990 | Tragardh et al. | 381/187 |
| 4,996,983 A | * | 3/1991 | AmRhein | 128/206.11 |
| 5,025,805 A | * | 6/1991 | Nutter | 128/207.18 |
| 5,042,933 A | * | 8/1991 | Lear | 351/111 |
| 5,117,818 A | * | 6/1992 | Palfy | 128/204.11 |
| 5,193,534 A | * | 3/1993 | Peppler | 128/207.18 |
| 5,336,179 A | * | 8/1994 | Ryan | 604/80 |
| 5,400,776 A | * | 3/1995 | Bartholomew | 128/200.24 |
| 5,438,979 A | * | 8/1995 | Johnson, Jr. et al. | 128/207.18 |
| 5,555,881 A | * | 9/1996 | Rogers et al. | 128/207.17 |
| 6,026,811 A | * | 2/2000 | Settle | 128/207.17 |

* cited by examiner

*Primary Examiner*—John G. Weiss
*Assistant Examiner*—Joseph F. Weiss, Jr.
(74) *Attorney, Agent, or Firm*—Jeffrey Weiss; Harry M. Weiss; Weiss, Moy & Harris, P.C.

(57) ABSTRACT

A retention device and method for retaining a gas delivery system provide improved safety and comfort for the recipient of oxygen or other gaseous mixture. The retention device includes a tube holder for maintaining a tension on a supply tube of a gas delivery system and an ear stop for transferring the tension of the supply tube to the back of an ear of the recipient. The device is generally molded from a flexible plastic material and includes a tube holder portion defining a cylindrical cavity therethrough for receiving and applying tension to a supply tube and an ear stop portion extending downwards from and end of said tube holder portion so that the tube holder portion may be placed over the recipient's ear and the ear stop placed behind the recipient's ear. A pair of the retention devices will generally be used, one for each ear. A channel or diverter may be included on the top of the tube holder portion to permit recipients wearing eyeglasses to comfortably use the device and the tube holder portion may extend backward from the ear stop to produce a cantilever effect that more effectively retains the ear stop against the recipient's ear. A radial opening may be provided in the tube holder portion for insertion of a supply tube where an end of the supply tube is not available. The opening may be closed and secured by forming mating surfaces in the walls defining the opening, by a flap to wrap around the opening or by other securing means.

22 Claims, 5 Drawing Sheets

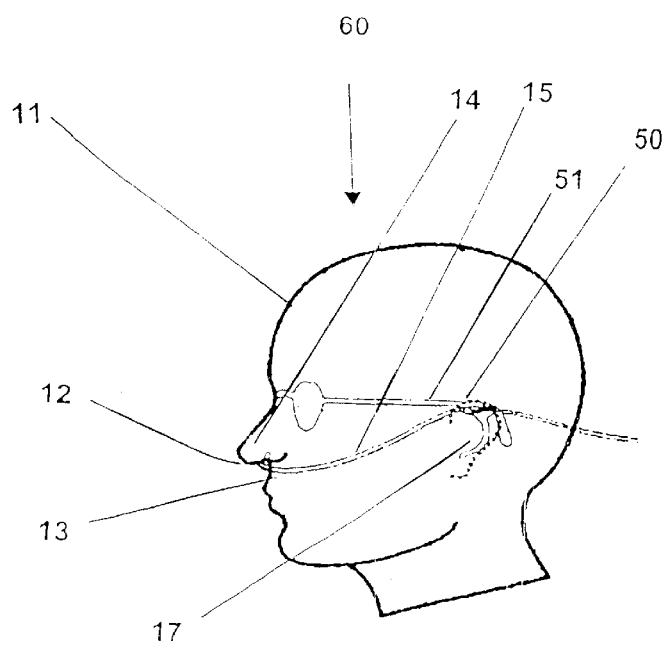
Fig. 2a
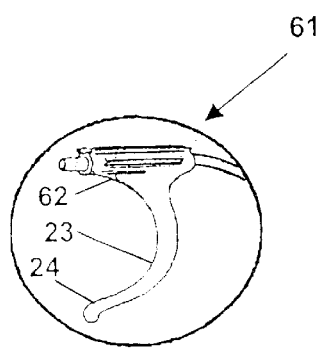
Fig. 2b
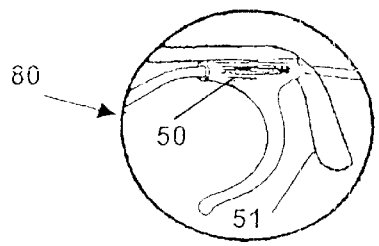
Fig. 2e
Fig. 2c
Fig. 2d
Fig. 2f

GAS DELIVERY SYSTEM RETENTION DEVICE AND METHOD FOR RETAINING A GAS DELIVERY SYSTEM

BACKGROUND OF THE INVENTION

1. Field of the Invention

The present invention relates generally to medical devices, and more specifically, to a device and method for retaining a gas delivery system on the head of a recipient of a gas.

2. Background of the Invention

It is often necessary to supply oxygen or a gas mixture to a hospitalized patient or to an individual requiring supplemental assistance with breathing or who is subjected to a low-oxygen environment.

Typically oxygen is administered by a nasal cannula system comprising flexible supply tubing terminating in a cannula having a pair of nipple ends that are inserted in the nostrils of the recipient. The supply tubing is routed along the cheeks and above the ears of the recipient and is brought under the ears and back together under recipient's chin by a sliding clip or a larger tube in which the two supply tubing is inserted. Tension is applied to the supply tubing by sliding the clip toward the recipient's head so that the nasal cannula is retained within the recipient's nostrils.

It is critical in some cases that oxygen be continuously supplied to the recipient, since it is possible that a recipient may worsen in medical status or may die without a continuous supply of oxygen. Therefore, the retention of the nasal cannula is critical, especially when the recipient is unattended and/or unconscious.

Present retention of the nasal cannula via the above-described arrangement is generally uncomfortable, as the amount of tension required on the tubing causes a great deal of pressure on the recipient's ears, chin and nose, making the recipient uncomfortable.

Further, due to comfort considerations, occasional removal or other need for adjustment of the nasal cannula system, a recipient often moves the sliding clip or tube to maintain sufficient tension on the supply tubes, if they are capable of making such adjustment. A recipient who is physically incapable of adjusting the nasal cannula system may nevertheless loosen the cannula accidentally by motion and whether capable or not, a recipient may loosen the cannula while sleeping. Therefore, frequent monitoring of persons using a nasal cannula is presently necessary for both the safety and comfort of the recipient.

Therefore, it is desirable to provide a nasal cannula retention device and method for retaining a nasal cannula that will ensure retention of the cannula during periods of unconsciousness or in the face of inability of a recipient to adjust the cannula retention device. It would further be desirable to provide a nasal cannula retention device and method for retaining a nasal cannula that are more comfortable for a recipient. It would also be desirable to provide a nasal cannula retention device and method for retaining a nasal cannula that require less frequent monitoring for patient comfort and safety.

SUMMARY OF THE INVENTION

The above objectives of retaining a nasal cannula to ensure retention during periods of unconsciousness or inability, provide more comfort and reduce monitoring requirements are achieved in a retention device and method for retaining a gas delivery system. The retention device includes at least one tube holder for maintaining tension on a supply tube of a gas delivery system and an ear stop for transferring tension to the rear of an ear of a recipient. The tube holder and ear stop may be molded or machined from a material to form a single continuous retention device.

The foregoing and other objectives, features, and advantages of the invention will be apparent from the following, more particular, description of the preferred embodiment of the invention, as illustrated in the accompanying drawings.

BRIEF DESCRIPTION OF THE DRAWINGS

FIGS. 2*a–f* is a pictorial diagram containing depictions of a retention device and system in accordance with alternative embodiments of the present invention.

DETAILED DESCRIPTION OF THE PREFERRED EMBODIMENTS

Figure 1A:
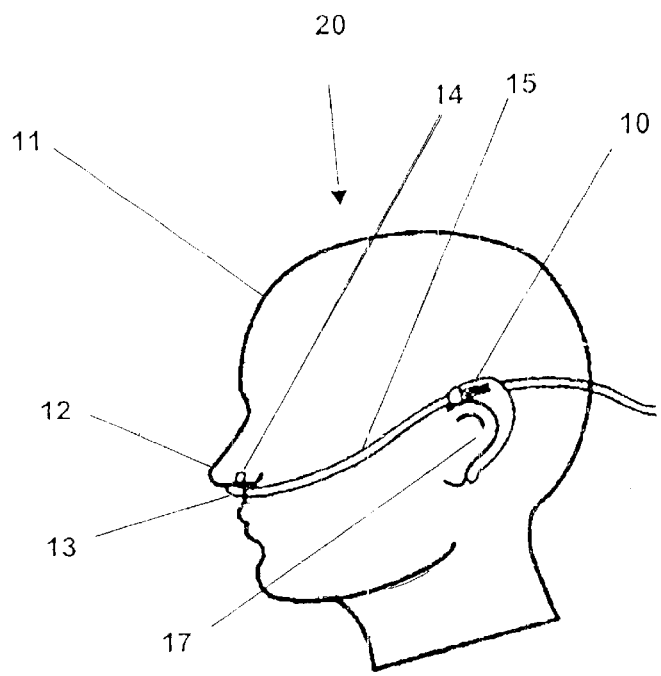
FIGS. 1*a–e* is a pictorial diagram containing depictions of a retention device and system in accordance with a first embodiment of the present invention.
Figure 1B:
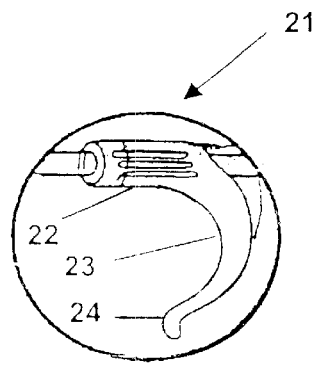
Figure 1C:
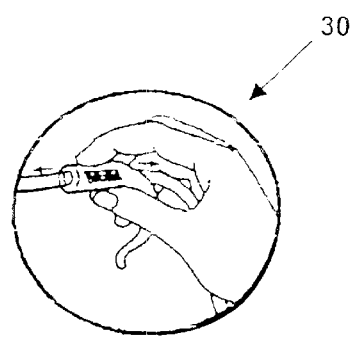
Figure 1E:
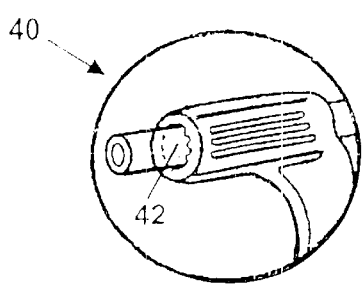
Figure 1D:
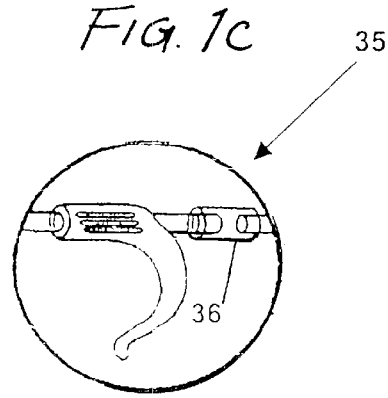

Referring now to the figures and in particular to FIG. 1, a nasal cannula retention device 10 and system 20 in accordance with an embodiment of the present invention are depicted. System 20 includes nasal cannula retention device 10, a pair of flexible supply tubes 15 on each side of an oxygen recipient's head 11 (one supply tube shown) and a nasal cannula 13 including nipples 14 for insertion in the nostrils of the recipient's nose 12. Nasal cannula retention device 10 is disposed around recipient's ear 17, and transfers tension from each supply tube 15 to the back of ear 17.

Detail 21 depicts features of nasal cannula retention device 10. Nasal cannula retention device 10 include two main portions: a tube holder 22 in the form of a sheath that defines a central cylindrical cavity and an ear stop 23 that transfers a force on tube holder 22 that is generated by tension on supply tube 15 to the back of recipient's ear 17. The embodiment depicted includes a curved surface to conform to the curvature of a recipient's ear 17 and a bulb 24 at the end of ear stop 23 to reduce the sharpness at the end of ear stop 23 for the comfort of recipient. Where the retention device 10 is to be used with an infant, including for example a "preemie," the shape of the tube holder 22 and ear stop 23 will likely need to be modified to accommodate the small size of the infant's ear.

Detail 30 shows a process of adjustment of nasal cannula retention device 10 along supply tube 15 whereby the tension on supply tube (and thus the force between nasal cannula 13 and recipient's nose 12) may be adjusted. The central cylindrical cavity may be formed with an oval cross section so that compression of a flexible tube holder 22 portion may ease the adjustment of detail 30 by reducing the frictional coupling of the inner wall of the cylindrical cavity temporarily by manually compressing the outer surface of tube holder 22 along the major axis of the oval cross-section.

Detail 35 depicts a coupler 36 that may be used for removal and attachment of nasal cannula retention device 10 by permitting separation of portions of supply tube 15 during attachment and removal of nasal cannula retention device 15. Detail 40 depicts features of the inner wall of cylindrical cavity 42. A plurality of splines directed toward the central axis of cylindrical cavity may be included to reduce the frictional coupling between tube holder 22 and supply tube 15 so that adjustment of tension on nasal cannula 13 is facilitated, along with facilitating attachment and removal of nasal cannula retention device 10 to and from supply tube 15.

In general, embodiments of the invention may include retention devices machined from wood or metal, but a flexible plastic retention device is preferred for comfort and ease of attachment and removal from supply tube 15. The plastic material used (which will typically be molded) should be hypo-allergenic and sufficiently rigid to permit ear stop 23 to transfer tension to back of recipient's ear, while permitting comfortable use with some flexure as will occur with movement of the recipient's head and compression if the weight of recipient's head rests on one recipient's ears. A thermoplastic elastomer material is preferred, though other materials may also be utilized.

Testing of nasal cannula retention device 10 and system 20 has been performed, resulting in positive indications of oxygen recipient comfort and ease of use by both the recipients and facility staff. Nasal cannula retention device 10 provides a mechanism whereby an oxygen recipient may reliably adjust the tension on a nasal cannula, retaining that tension after waking movement and during sleep.

Referring now to FIG. 2, a nasal cannula retention device 50 and system 60 in accordance with an alternative embodiment of the present invention are depicted. The alternative embodiments provide added comfort and usability of the invention for oxygen recipients wearing eyeglasses. System 60 includes nasal cannula retention device 50, a pair of flexible supply tubes 15 on each side of an oxygen recipient's head 11 (one supply tube shown) and a nasal cannula 13 including nipples 14 for insertion in the nostrils of the recipient's nose 12. Nasal cannula retention device 50 is disposed around recipient's ear 17, with a pair of eyeglasses 51 worn by recipient disposed thereon. Nasal cannula retention device 50 tranfers tension from each supply tube 15 to the back of ear 17.

Detail 61 depicts features of nasal cannula retention device 50. Nasal cannula retention device 50 include two main portions: a tube holder 62 in the form of a sheath that defines a central cylindrical cavity and including a means for either deflecting or holding an earpiece of eyeglasses 51, and an ear stop 23 that transfers a force on tube holder 62 that is generated by tension on supply tube 15 to the back of recipient's ear 17. The embodiment depicted includes a curved surface to conform to the curvature of a recipient's ear 17 and a bulb 24 at the end of ear stop 23 to reduce the sharpness at the end of ear stop 23 for the comfort of recipient.

Detail 70 shows a process of adjustment of nasal cannula retention device 50 along supply tube 15 whereby the tension on supply tube (and thus the force between nasal cannula 13 and recipient's nose 12) may be adjusted. The central cylindrical cavity may be formed with an oval cross section so that compression of a flexible tube holder 62 portion may ease the adjustment of detail 70 by reducing the frictional coupling of the inner wall of the cylindrical cavity temporarily by manually compressing the outer surface of tube holder 22 along the major axis of the oval cross-section.

Detail 75 depicts a second alternative embodiment of nasal cannula retention device 50A that provides a diverter 76 for an earpiece of eyeglasses 51. When the recipient wears eyeglasses, the narrowed top of diverter 76 permits the placement of an eyeglass earpiece to either side of the top (tip portion) of diverter 76, thus retaining the eyeglass earpiece either between diverter 76 and the outer portion of recipient's ear or between diverter 76 and recipient's head. The diverter 76 provides the added benefit of increased comfort to the wearer even where glasses are not worn. Where, for example, a recipient wishes to lay his or her head on a pillow, pressure on the ear proximate the flexible tube holder can cause discomfort, with the interior of the ear surface being impinged by the flexible tube holder. By limiting the size of the flexible tube holder with the diverter 76, the amount of any discomfort should be lessened. In general, the diverter may also be used in situations where it is desirable to reduce pressure on the ear by reducing the amount of material present at the top of tube holder. Thus, the diverter feature as depicted may be used with or without eyeglasses to improve the comfort of recipient.

Detail 85 depicts details of the alternative embodiment of nasal cannula retention device 50 that provides a channel 86 formed between two exterior splines to receive an earpiece of eyeglasses 51. When the recipient wears eyeglasses, an earpiece of the eyeglasses is placed within channel 86, thus retaining the eyeglasses. Detail 80 shows nasal cannula retention device 50 with eyeglass 51 earpiece in a mounted configuration.

As can be seen from a comparison of the embodiments of FIG. 1 and FIG. 2, in one embodiment the rearmost portion of the flexible tube holder 22 terminates at the topmost portion of the ear stop 23. In another embodiment, the rearmost portion of the tube holder 62 extends beyond the topmost portion of the ear stop 23. The reason for this latter configuration is that it alters the center of gravity of the device, providing a cantilever whereby more of the tension from the supply tubes 15 is transferred to the back of the recipient's ear 17, increasing security and lessening the risk that the device could become accidentally dislodged.

Figure 3A:
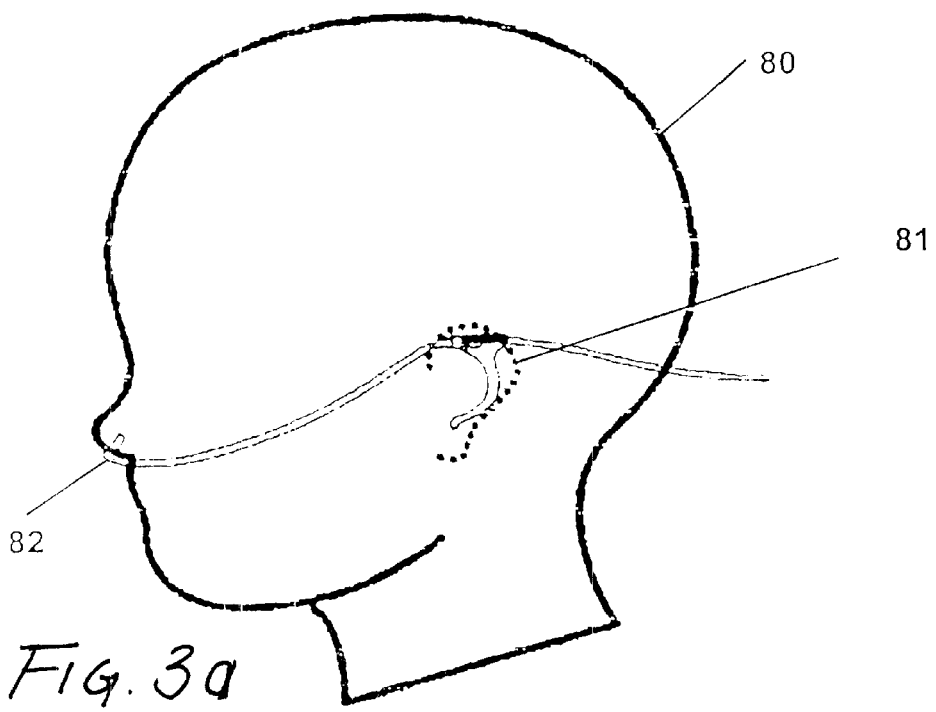
FIGS. 3*a–c* is a pictorial diagram containing depictions of a retention device and system in accordance with alternative embodiments of the present invention.
Figures 3B, 3C:
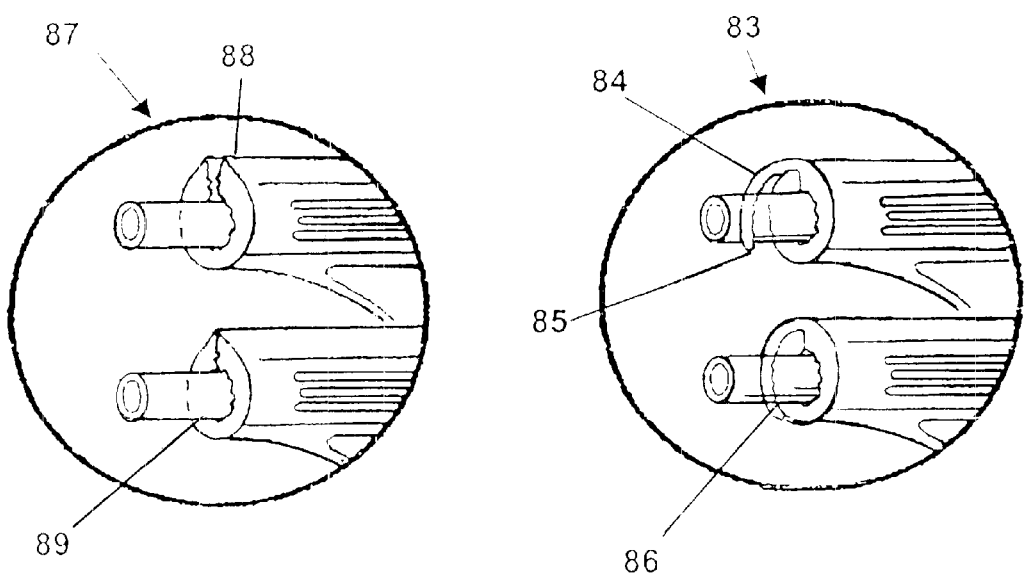

Referring now to FIG. 3, a nasal cannula 82 retention device 81, adapted for use with a prematurely-born infant is shown. The features are as described above for other nasal cannula retention devices, but are dimensioned for the average shape and curvature of the infant's head 80. Other sizes and shapes of nasal cannula retention devices 81 may be manufactured for age and size ranges so that a proper fit and retention are achieved.

Detail 87 depicts a retention device for attachment to an existing gas supply tube where it is not desirable to slide the gas supply tube through a closed central cylindrical cavity. An opening 88 at the top of cavity is provided in the tube holder portion of the retention device and the opposing surfaces forming opening 88 can be more securely mated by matching corrugations on either side of opening 88. Other suitable mating surfaces may be formed in tube holder and the corrugations depicted are only illustrative of one example.

Detail 83 also depicts a retention device for attachment to an existing gas supply tube, providing an alternative "wrap-around" mechanism for attaching the retention device to a gas supply tube. In the open position 84, an extension 85 is retracted from a mating outside surface of the tube holder and in the closed position 86, the extension wraps around the outside surface and is secured via the mating surface, which may be a surface with matching corrugations or other suitable securing mechanism.

Figure 4A:
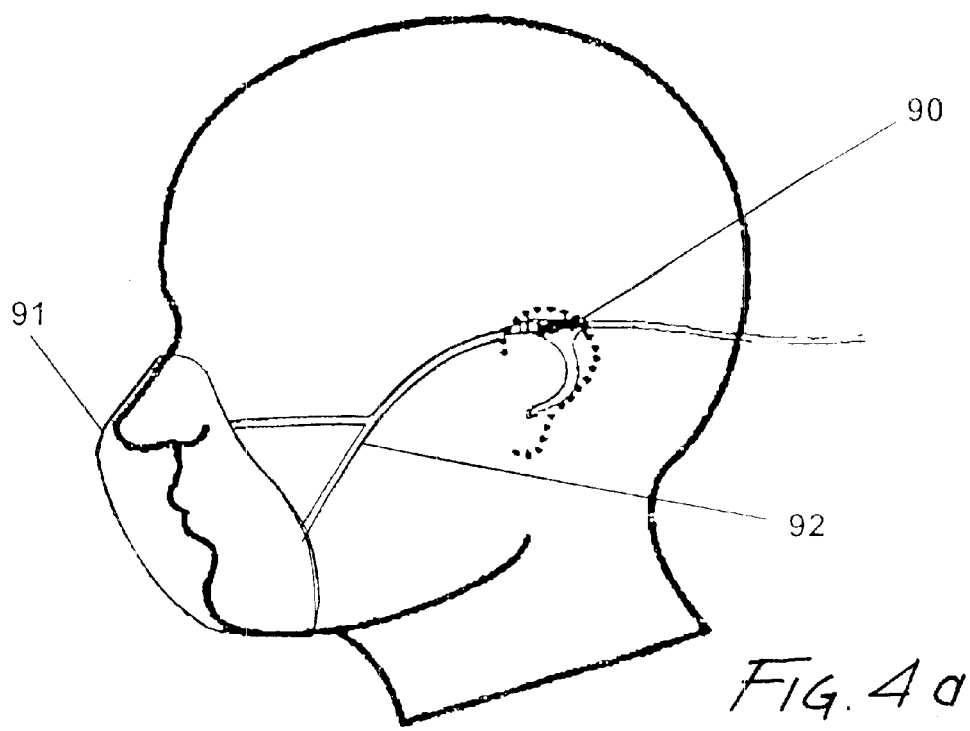
FIGS. 4*a–b* is a pictorial diagram containing depictions of a retention device and system in accordance with alternative embodiments of the present invention.
Figure 4B:
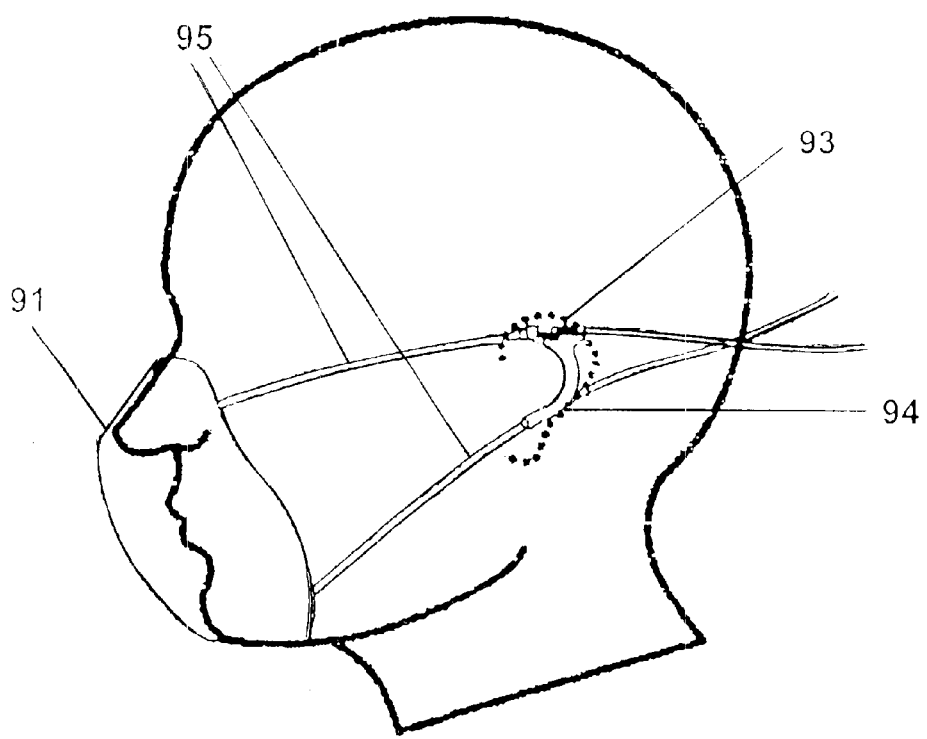

Referring now to FIG. 4, retention devices as employed in retaining an oxygen mask 91, are shown. The topmost drawing depicts a retention device 90 for retaining a gas tube set that converges in a "Y" 92 prior to the attachment point of retention device 90. The design of retention device 90 is as described above for the nasal cannula retention device, as only one gas tube must be retained on each side of the recipient's head. The "Y" 92 configuration provides two gas tubes connecting to oxygen mask 91 on each side of the recipient's head, stabilizing and securing oxygen mask 91.

The bottommost drawing in FIG. 4 shows an alternative retention device 93, adapted for securing oxygen mask 91 via a pair of gas supply tubes 95. One gas supply tube is directed over the recipient's ear and one gas supply tune is directed under the recipient's ear on either side of recipient's head. A second tube holder 94 is incorporated at the bottom of retention device 93 and may incorporated the ovoid inner cavity, splines and other devices suitable for use in the upper tube holder of the above-described embodiments of the present invention.

Figure 5:
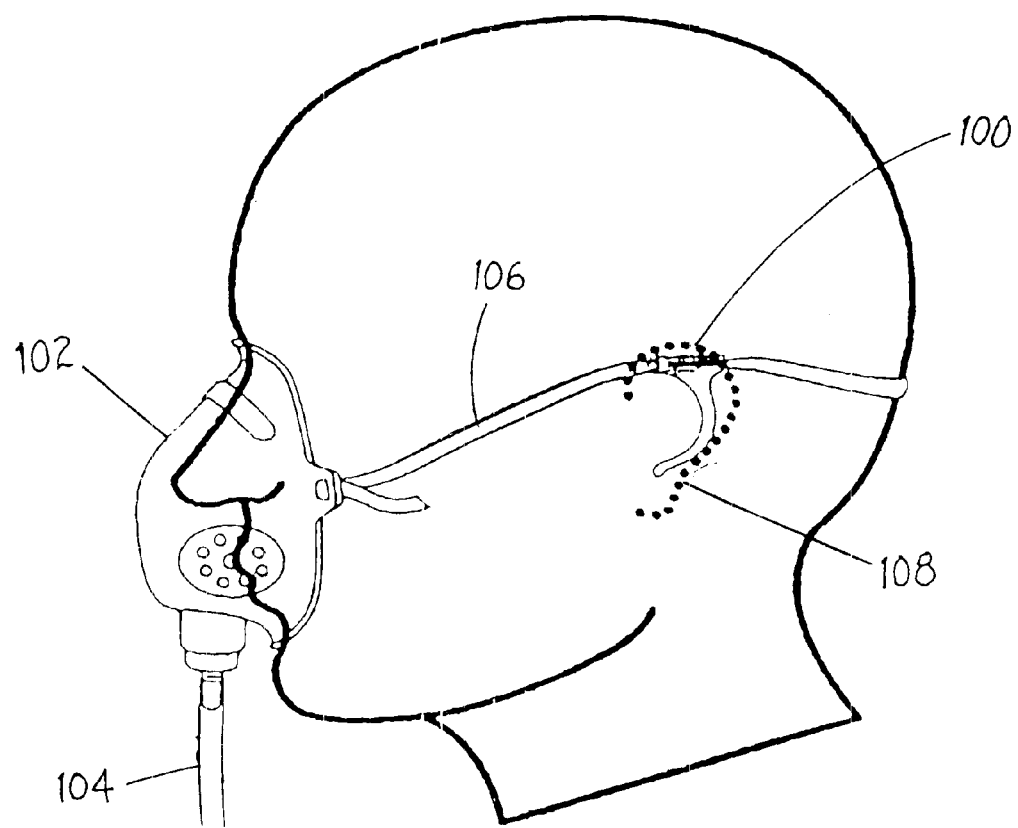
FIG. 5 is a pictorial diagram depicting use of the retention device and system in combination with a mask and the mask's head securing straps.

Referring now to FIG. 5, an alternative retention device 100, adapted for securing oxygen mask 102, is shown. In this embodiment, oxygen mask 102 receives its gas supply through a bottom portion thereof, through gas supply tube 104. An elastic strap 106 secures the oxygen mask 102 in position on the recipient's head. A strap holder 108 is secured to the strap 106 on each side of the recipient's head, and positioned on the recipient's ear in the manner described above While the depictions of FIG. 4 are described as applying to an oxygen mask, it should be understood that the retention devices and masks retention systems of the present invention are suitable for use with other gases and delivery systems, as well as filters and other breathing apparatus. The invention may also be applied to securing other devices to a patient's head, such as securing dental bridgework during and after installation.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A retention device for retaining a gas delivery system on a patient's head, comprising:
    a tube holder portion having a first end and a second end and a cylindrical tube having a length therebetween, said cylindrical tube defining a cylindrical cavity adapted to engage a supply tube;
    said tube holder portion further comprising a first tubular section and a second tubular section, the first tubular section adapted to engage the supply tube and maintain a tension upon the supply tube, and the second tubular section being adapted to engage a superior portion of an auricle proximate a helix portion of the auricle;
    said first tubular section including an inner tubular wall extending from said first end to said second end having an ovoid shape in cross section, said ovoid shape enabling said inner tubular wall to frictionally engage and maintain said tension on the supply tube passing therethrough;
    an ear stop portion having a first end and a second end and a length therebetween with the first end being connected to the tube holder and the second end being adapted to engage an inferior portion of an auricle proximate a lobule portion of the auricle;
    said tube holder portion and ear stop portion forming a substantially 7-shaped structure, wherein when in use said tube holder portion forms a horizontal leg of the 7-shaped structure and the ear stop portion forms an angled vertical leg of the 7-shaped structure;
    wherein when in use force on the tube generated by the tension between the tube holder portion's first tubular section and the tube is translated to the ear stop portion and wherein the supply tube's direction of travel is not redirected by the tube holder.

2. The retention device of claim 1, wherein said tube holder and said ear stop form a contiguous molded flexible plastic device.

3. The retention device of claim 1, wherein said tube holder further comprises a plurality of splines extending from an inner surface of said cylindrical cavity toward a central axis of said cylindrical cavity whereby said tension may be maintained on said supply tube.

4. The retention device of claim 1, wherein said tube holder is a flexible plastic tube holder, and whereby said ovoid may be compressed to a substantially circular cross-section to reduce said friction coupling, facilitating movement of said supply tube relative to said tube holder.

5. The retention device of claim 4, wherein said tube holder further comprises a plurality of splines extending from an inner surface of said cylindrical cavity toward a central axis of said cylindrical cavity whereby said tension may be maintained on said supply tube, and wherein compression of said ovoid moves said splines to reduce said friction coupling.

6. The retention device of claim 1, wherein a pair of radial walls of said tube holder define a radial opening in said cylindrical cavity whereby the supply tube may be inserted therethrough.

7. The retention device of claim 6, wherein said radial walls are formed with corresponding mating surfaces, whereby said radial opening may be closed and secured.

8. The retention device of claim 6, wherein said tube holder further comprises an extension of a given one of said radial walls having a thickness of less than the thickness of said given radial wall and conforming with an exterior surface of said tube holder, whereby said extension may be wrapped around said exterior surface of said tube holder for closing said radial opening.

9. The retention device of claim 8, wherein said exterior surface of said tube holder and an interior surface of said extension are formed with corresponding mating surfaces, whereby said radial opening may be closed and secured.

10. The retention device of claim 1, wherein said ear stop comprises a substantially semi-circular inferiorly curved leg conforming to the patient's posterior auricle region.

11. The retention device of claim 10, wherein said ear stop further comprises a bulb at said end portion thereof.

12. The retention device of claim 1, wherein an exterior portion of said tube holder defines a groove for admitting a portion of an arm of a pair of eyeglasses worn by the patient.

13. The retention device of claim 1, wherein an exterior portion of said tube holder defines a ridge for deflecting to a side of said ridge a portion of an arm of a pair of eyeglasses worn by to a side of said ridge.

14. The retention device of claim 1, wherein said tube holder extends past said ear stop to provide a cantilever whereby more of said tension is transferred to the patient's pooterior auricle region.

15. A method for retaining a gas delivery system on a patient's head, comprising:
    a step of applying a tension to a supply tube of said gas delivery system;
    wherein the step of applying tension to said supply tube further comprises a step of providing a retention device comprising a tube holder portion having a first end and a second end and a cylindrical tube having a length therebetween, said cylindrical tube defining a cylindrical cavity adapted to engage a supply tube;

said tube holder portion further comprising a first tubular section and a second tubular section, the first tubular section adapted to engage the supply tube and maintain a tension upon the supply tube, and the second tubular section being adapted to engage a superior portion of an auricle proximate a helix portion of the auricle;

said first tubular section including an inner tubular wall extending from said first end to said second end having an ovoid shape in cross section; said ovoid shape enabling said inner tubular wall to frictionally engage and maintain said tension on the supply tube passing therethrough;

said method further comprising a step of transferring force on the supply tube generated by the tension between the inner tubular wall and the supply tube to a posterior region of the auricle of the patient;

wherein the step of transferring said force further comprises a step of providing an car stop;

an ear stop portion having a first end and a second end and a length therebetween with the first end being connected to the tube holder and the second end being adapted to engage an inferior portion of an auricle proximate a lobule portion of the auricle;

said tube holder portion and ear stop portion forming a substantially 7-shaped structure wherein when in use said tube holder portion forms a horizontal leg of the 7-shaped structure and the ear stop portion forms an angled vertical leg of the 7-shaped structure;

wherein when in use force on the tube generated by the tension between the tube holder portion's first tubular section and the tube is translated to the ear stop portion and wherein the supply tube's direction of travel is not redirected by the tube holder.

16. The method of claim 15, further comprising facilitating extraction of said supply tube by compressing a cross-section of said tube holder whereby said ovoid cross-section is rendered substantially circular.

17. The method of claim 15, wherein said tube holder includes splines for contacting said supply tube and wherein said transferring is performed through said splines.

18. The method of claim 15, wherein said transferring is performed along a substantially semi-circular curved surface conforming to the patients posterior auricle region.

19. The method of claim 15, further comprising inserting a portion of an arm of a pair of eyeglasses worn by said recipient into a groove in a retention device.

20. The method of claim 15, further comprising deflecting a portion of an arm of a pair of eyeglasses worn by the patient to a side of a retention device.

21. The method of claim 15, wherein said transferring comprises cantilevering said tube holder so that more of said tension is transferred to the patient posterior auricle region.

22. A retention device for retaining a gas delivery system on a patient's head, comprising:

a tube holder portion having a first end and a second end and a cylindrical tube having a length therebetween, said cylindrical tube defining a cylindrical cavity adapted to engage a supply tube;

said tube holder portion further comprising a first tubular section and a second tubular section, the first tubular section adapted to engage the supply tube and maintain a tension upon the supply tube, and the second tubular section being adapted to engage a superior portion of an auricle proximate a helix portion of the auricle;

wherein said first tubular section further comprises a plurality of splines extending from an inner surface of said cylindrical cavity toward a central axis of said cylindrical cavity whereby said a tension may be maintained on said supply tube;

an ear stop portion having a first end and a second end and a length therebetween with the first end being connected to the tube holder and the second end being adapted to engage an inferior portion of an auricle proximate a lobule portion of the auricle;

said tube holder portion and ear stop portion forming a substantially a substantially 7-shaped structure, wherein when in use said tube holder portion forms a horizontal leg of the 7-shaped structure and the ear stop portion forms an angled vertical leg of the 7-shaped structure;

wherein when in use force on the tube generated by the tension between the tube holder portion's first tubular section and the tube is translated to the ear stop portion and wherein the supply tube's direction of travel is not redirected by the tube holder.

* * * * *